(12) United States Patent
Naccarato et al.

(10) Patent No.: US 6,617,146 B1
(45) Date of Patent: Sep. 9, 2003

(54) METHOD AND APPARATUS FOR AUTOMATICALLY INOCULATING CULTURE MEDIA WITH BACTERIAL SPECIMENS FROM SPECIMEN CONTAINERS

(75) Inventors: Frank Naccarato, Toronto (CA); Anne M. C. Bornath, King City (CA); Georgeta Mazilu, West Porters Lake (CA)

(73) Assignee: Canadian Space Agency, Saint-Hubert (CA)

( * ) Notice: Subject to any disclaimer, the term of this patent is extended or adjusted under 35 U.S.C. 154(b) by 0 days.

(21) Appl. No.: 09/381,209

(22) PCT Filed: Mar. 17, 1998

(86) PCT No.: PCT/CA98/00212

§ 371 (c)(1), (2), (4) Date: Dec. 9, 1999

(87) PCT Pub. No.: WO98/41610

PCT Pub. Date: Sep. 24, 1998

(30) Foreign Application Priority Data

Mar. 17, 1997 (CA) .............................................. 2.200.116
Jan. 16, 1998 (CA) .............................................. 2.227.317

(51) Int. Cl.[7] .......................... C12M 1/00; C12M 1/26; C12N 1/00; C12N 1/12; C12N 1/20
(52) U.S. Cl. ................. 435/243; 435/252.1; 435/283.1; 435/283.3; 435/309.1
(58) Field of Search .............................. 435/41, 235.1, 435/325, 243, 283.1, 286.3, 288.3, 288.4, 288.5, 304.1, 307.1, 309.1, 309.2, 810, 252.1, 283.3

(56) References Cited

U.S. PATENT DOCUMENTS

| | | | | |
|---|---|---|---|---|
| 3,632,478 A | * | 1/1972 | Fink | 195/139 |
| 3,660,243 A | * | 5/1972 | Young | 195/139 |
| 4,981,802 A | * | 1/1991 | Wylie et al. | 435/294 |
| 5,756,304 A | * | 5/1998 | Jovanovich | 435/34 |

FOREIGN PATENT DOCUMENTS

| | | | |
|---|---|---|---|
| EP | 0195088 A | * | 9/1986 |
| EP | 0737741 A | * | 10/1996 |
| FR | 2527221 A | * | 11/1983 |
| WO | WO 94/9452 A | * | 9/1994 |

* cited by examiner

*Primary Examiner*—David M. Naff
*Assistant Examiner*—Deborah K. Ware
(74) *Attorney, Agent, or Firm*—Kathleen E. Marsman; Borden Ladner Gervais LLP

(57) ABSTRACT

A method and system are provided for automatically positioning specimen containers and culture medium containers and transferring specimen samples from the containers to the culture medium. The samples are positioned at predetermined locations, and a sample is automatically streaked in a pattern on the culture medium after deposition of the sample. A means is also provided for establishing the predetermined locations by recording a position of a deposit location in a memory as deposit location data. Biological specimens such as a sample of bacteria are used in the method and system.

27 Claims, 15 Drawing Sheets

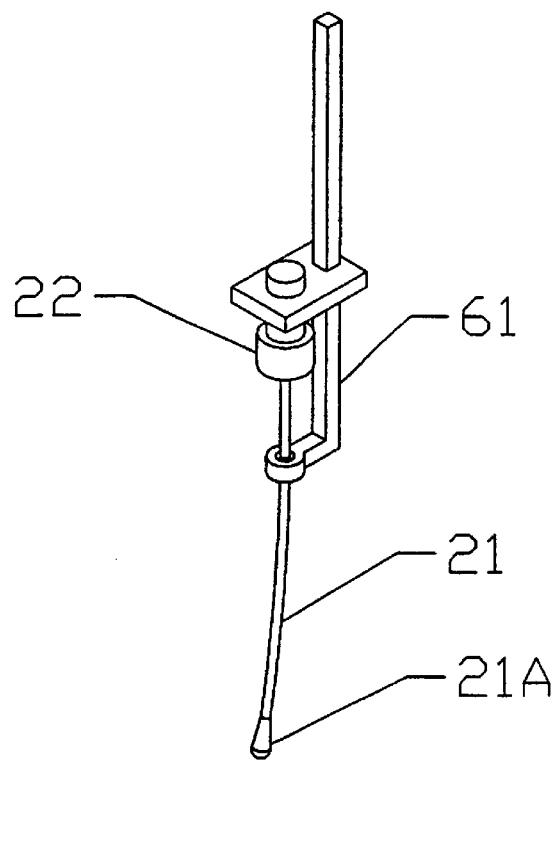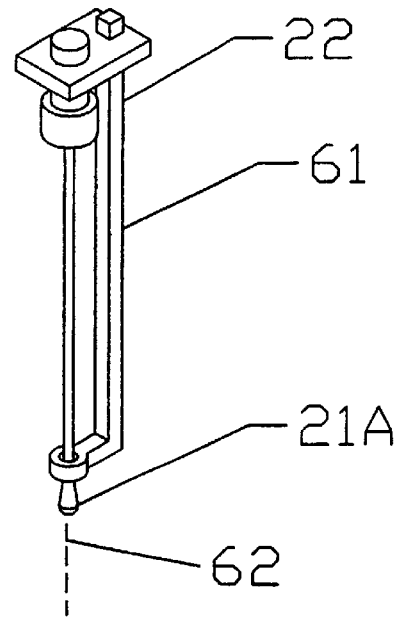
Figure 22A  Figure 22B
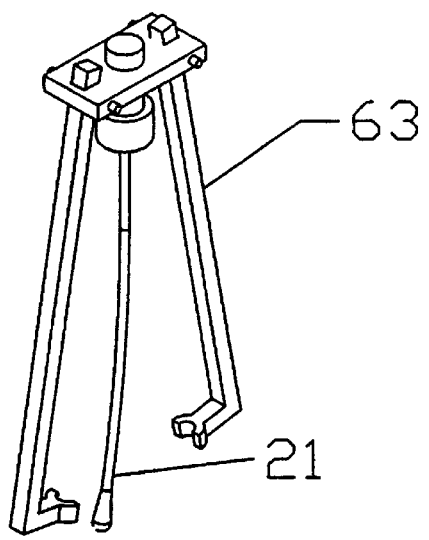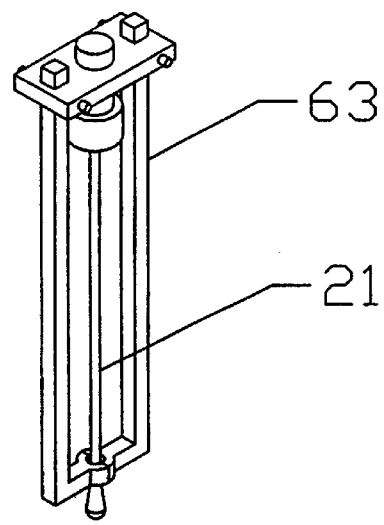
Figure 23A  Figure 23B

METHOD AND APPARATUS FOR AUTOMATICALLY INOCULATING CULTURE MEDIA WITH BACTERIAL SPECIMENS FROM SPECIMEN CONTAINERS

FIELD OF THE INVENTION

This invention relates to an apparatus and method for automatically transferring bacterial specimens from specimen containers to the surface of culture medium plates, and to streaking such bacterial samples in programmable patterns to produce isolated bacterial colonies. In particular, it provides for the precise deposition of an inoculant at a specific location on the surface of a culturing medium, and the subsequent re-entry of a streaking tool at this same location to effect streaking. It further provides a versatile system for varying the streaking procedure in accordance with the specimen being treated. This invention also relates to an apparatus and method for automatically removing the top of either "jar-type" specimen container or a "swab-type" container while simultaneously identifying the specimen.

BACKGROUND TO THE INVENTION

The isolation and identification of a sample of a bacterial specimen has for many years involved the inoculation of the sample onto a culture medium. The type of culture medium used and the method by which it is placed on the culture medium depends on the type of specimen being handled.

This invention relates in one aspect to two types of specimen containers. One type of specimen container, the "swab-type", consists of a stylus- or wand-like stem attached to a cap removably fitted onto a separate, test-tube like container. A swab fixed at the opposite end of the stem from the cap is coated with and carries the bacterial specimen during transfer to the cultivating medium. The other type of specimen container, the "jar-type", consists of a jar- or bottle-like vessel containing a liquid specimen, such as urine, a portion of which is to be transferred to inoculate the cultivating medium.

The receptacle containing the swab is typically a transparent tube having a closed end and an open end providing a narrow mouth. The swab shaft carries its absorbent pad —the swab tip— at the outer end of the stem remote from the cap end. While the stem extends into the tube from the cap when the cap is in place on the tube, variations in manufacturing may cause the stem to be deflected sideways. Hence, upon removal of the swab stem from the tube, the stem may deflect from alignment with the central axis of the cap causing the displacement of the swab tip sideways. The precise location of the swab relative to the cap and the axis of the cap will then be unknown.

Inoculation from a "swab-type" container requires identification of the specimen type, removal of the cap (with the stem and swab attached) from the receptacle and rolling the swab end (which is coated with the specimen) over a portion of the surface on a culture medium which is suited to the specimen. This transfer must occur at a specific deposit location and the sides of the swab should be equally exposed to the surface of the cultivating medium, without disrupting the surface, during transfer of bacteria to the deposit location. If the swab stem is bent, this operation is difficult to effect through automation.

An object of this invention is to effect inoculation of the cultivating medium at a deposit location whose position is recorded, followed by effecting streaking automatically, using the recorded deposit location to guide an automated streaking tool.

After inoculation occurs the swab is normally returned to its original container. In doing so the swab must be aligned with the mouth of the test-tube to prevent contamination of the exterior portion of the tube. This alignment must be arranged even when the swab stem is bent.

Inoculation from a "jar-type" container requires removal of the cap, extraction of a specified amount of liquid, e.g. urine, and placement of an amount of liquid onto the deposit location on the culture medium's surface. The container with its remaining liquid is then recapped and conveyed away for storage.

Inoculation from a "jar-type" container requires identification of the specimen (as by reading markings on the outside surface of the container), removal of the cap, extraction of a specified amount of urine, placement of that amount onto a defined area on the appropriate culture medium and recapping the jar. This procedure is time consuming, inconsistent and biohazardous. Automating the entire procedure would address all three of these concerns. Two critical parts of the inoculating process for the "jar-type" specimen container are the uncapping of the specimen container and the reading of the data imprinted on the container.

The isolation and identification of a specimen requires that the specimen sample be distributed or spread over the culture medium—"streaked"—in a one of several prescribed patterns that is correlated to the specific specimen. These patterns must provide an increasing dilution of the sample and are effected by a streaking tool. Once so streaked the prepared medium plates can then be incubated to promote bacterial growth. This bacterial growth can then be examined or subjected to further tests for isolation or identification of the bacteria type(s) present in the specimen.

Proper preparation of the media plates is biohazardous, time consuming and difficult to perform manually in a consistent manner. It is also difficult to maintain consistency between the techniques used by different technicians or even between different samples prepared by the same technician at different times.

An object of this invention is therefore to provide a method and apparatus for inoculating medical specimens from either the "swab-type" or "jar-type" containers onto culture media which closely simulates the effect of established manual procedures, but with improved consistency, accuracy and safety.

A further objective is to provide a method and apparatus for removing a specimen swab from a container, and to provide for reading data on the container.

A further objective is to provide a method in which a specimen swab, e.g. an elongate element, which is somewhat bent from its nominal position may be properly applied to the surface of a cultivating medium and then be reinserted into its originating receptable consistently and accurately.

A further object of this invention is to provide a method and apparatus for streaking bacterial samples in programmable patterns corresponding to the actual specimen being evaluated, which closely simulates the effect of established manual procedures, but with improved consistency, accuracy and safety.

Yet a further objective is to provide an efficient method and apparatus in which the cap of a jar-type container may be removed in parallel with reading data that has been imprinted, encoded or otherwise embedded on the container. An additional objective is to provide a method and apparatus in which the existence of a sufficient amount of liquid specimen in the container may be verified.

The invention in its general form will first be described, and then its implementation in terms of specific embodiments will be detailed with reference to the drawings following hereafter. These embodiments are intended to demonstrate the principle of the invention, and the manner of its implementation. The invention in its broadest and more specific forms will then be further described, and defined, in each of the individual claims which conclude this Specification.

SUMMARY OF THE INVENTION

A preferred embodiment of this invention provides an automated overall specimen container transport, handling and inoculating system which integrates and improves standard procedures and techniques for transferring bacteria to a cultivating medium, followed by streaking of such bacteria on such medium using automated means. Thus a specimen delivery system conveys a sample specimen to a deposit location on a culture medium, recording the location of the deposit location in a memory. A streaking mechanism then effects streaking using the recorded deposit location data to guide the streaking tool.

According to a further feature of the invention, the mechanism of the system may dispense culture media as called for by the specimen's embedded data and identify or label each dispensed container of media so that it can be correlated with its corresponding specimen. A sample of the bacterial specimen on a specimen carrier e.g., a swab or pipette, is then transferred to the culture medium by a specimen sample delivery system or "specimen delivery system". Streaking is thereafter effected in accordance with the procedure appropriate for each specific specimen.

As indicated, a special feature of the invention is that a specimen delivery system which is computer controlled is used to convey the specimen from its original container to a deposit location on the culture medium. A computer controlled streaking tool carried by a streaking mechanism is then directed to the same deposit location based upon digitally stored data corresponding to the precise position of such deposit location. The streaking tool may then engage the culture medium and effect streaking in accordance with the pattern suited for the specific specimen with which the culture medium has been inoculated.

The specimen delivery system brings the specimen carrier with its bacterial sample in contact with the culture medium in a controlled manner which ensures that the bacteria are properly deposited at the deposit location. For "swab-type" specimens comprising a stylus- or wand-like swab stem attached to a cap and carrying a swab coated with the bacterial specimen, the swab is so "fixtured" that when it is brought into contact with its corresponding culture medium, the transfer of bacteria occurs at the deposit location in the correct manner.

To achieve such fixturing of the swab according to one feature of the invention, a capped swab-containing receptacle is first placed into a holding fixture by a robot manipulator. The same manipulator then grasps the cap and withdraws it and the attached swab stem from the mouth of the receptacle. The swab and swab stem are then presented to a tip location device. The exact location of the swab located at the stem tip and its orientation with respect to the cap's position is determined by a visual examination effected by the tip location device. This exact tip location with respect to the end effector of the grasping manipulator is then stored in a digital memory to subsequently be used to control the specimen delivery system in positioning the swab on the culture medium at the deposit location in order to properly inoculate that medium. Then the specimen delivery system is used to reinsert the swab into the receptacle, again using the digitally stored data defining the location of the swab at the stem tip to ensure that the swab passes into the mouth of its container without contaminating its rim or exterior surface.

In one embodiment, the swab tip is located using a camera and a single back-lighted surface. A 90° rotation about the axis of the element is effected and two images are taken by the camera to establish the location of the swab tip. In another embodiment, the swab tip is located using a single camera image frame, two mirrors, and two back-lighted surfaces whereby two separate views of the swab tip are effected simultaneously. In yet another embodiment, a laser range camera may be used to scan and establish the location of the swab tip. From these measurement procedures the location of the tip is determined and stored in the memory of the digital controller.

The swab tip is then carried by the specimen positioning system to the deposit location whereat the outer surface of the swab is rolled against the surface of the culture medium to transfer bacteria to the deposit location. During this transfer, the swab in one variant is fixtured to maintain the required degree of contact with the culture medium surface by the action of the specimen delivery system in adjusting the location of the cap laterally while the cap is being rotated. This adjustment is effected using the data for the location of the swab tip with respect to the cap, as stored in the digital memory.

Rather than so controlling the position of the cap while it is being rotated, the cap may be rotated at a stationary location if the swab tip is mechanically fixtured to ensure that it is positioned along the axis of rotation of the cap. This may be effected by extending a guide, such as a wire with a loop, from the specimen delivery system so that the loop guides the swab tip into alignment with the axis of rotation of the cap during transfer of bacteria to the culture medium.

For "jar-type" containers, once its cap is removed, the specimen delivery system uses a pipetting tool as the specimen sample carrier to extract a volume of liquid from the open container and then deposit a volume of this liquid onto the surface of the culture medium at the deposit location. Again, the specimen carrier —the pipetting tool—is so fixtured that the robot manipulator as the specimen delivery system places the specimen precisely at the deposit location. As previously described, the position of the deposit location in space is recorded in a digital memory for subsequent use in further operations.

To present the jar-type containers to the specimen positioning system, a container manipulating device grasps the cap of the specimen container while the container is rotated by a rotating jar holder. The container manipulating device raises and removes the cap of the specimen container to one side once the rotating holder for the container has rotated it sufficiently so as to cause the cap and the receptacle to disengage. During this rotational motion, a scanning device located to one side of the holder/reader platform may conveniently read specimen-identifying indicia that has been previously imprinted, encoded or otherwise embedded on the side of the specimen container. A similar procedure may also be provided for reading indicia carried on the side of tubes containing swabs.

Provision is included for verifying the amount of specimen in the container. Provision is also provided for replacing the cap on the receptacle of the specimen container after the sample has been extracted.

As a particularly convenient arrangement, a jar-type container may be delivered to its lid-opening station on a conveyor, and the removal of the lid and extraction of a specimen sample may be effected with the jar container remaining on and supported by the conveyor.

Once a sample of bacteria has been transferred to the deposit location, streaking is then effected by a streaking tool which is carried by the streaking mechanism to the deposit location. The control system for the streaking tool uses digitally stored data in order to carry the streaking tool to the deposit location, optionally using a common robotic manipulator. The streaking pattern then effected is computer controlled to correspond with the identity of the specimen as obtained from the specimen container.

The deposit location, whether by application from a swab container or jar-type container can be stored in a suitable "memory" plus also specimen identification.

The streaking apparatus of the invention with its computer control system is versatile and may adopt a full range of streaking patterns. This feature, combined with the capacity to accept specimens in differing types of containers renders the apparatus of the invention highly versatile.

The foregoing summaries the principal features of the invention and some of its optional aspects. The invention may be further understood by the description of the preferred embodiments, in conjunction with the drawings, which now follow.

SUMMARY OF THE FIGURES

FIGS. 22A and 22B depict a fixturing mechanism for the swab tip which is slid-down the swab stem.

FIGS. 23A and 23B depict a fixturing mechanism for the swab tip using a clam-type grasping action.

FIGS. 24A, 24B and 25C show the transfer to a culture medium of a bacterial specimen from a swab tip fixtured as shown in FIGS. 22A and 22B.

FIGS. 25A, 25B and 25C show the transfer to a culture medium of a bacterial specimen from a swab tip fixtured by controlled displacement of the holder grasping the swab cap.

DESCRIPTION OF THE PREFERRED EMBODIMENT

Figure 1A:
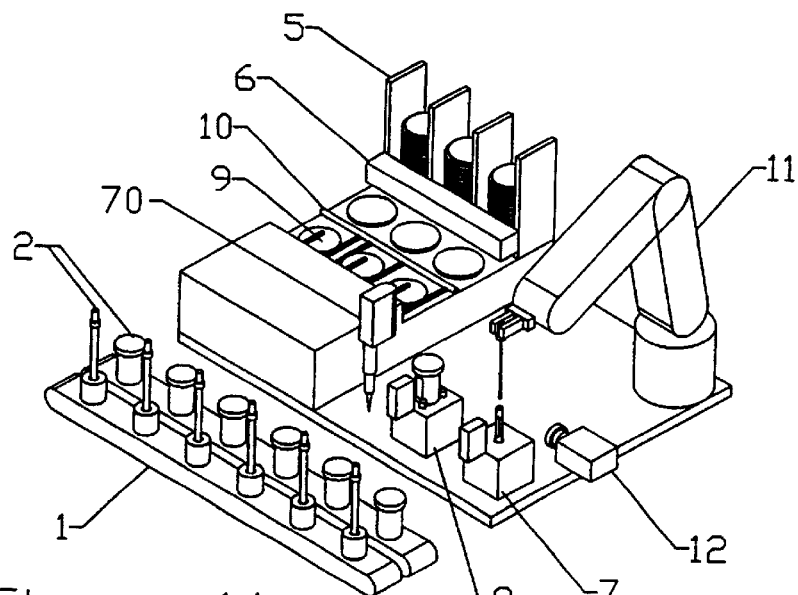
FIG. 1A is a pictorial view of a combined inoculation and streaking apparatus for accepting samples in both swab-type and jar-type container formats.
Figure 1C:
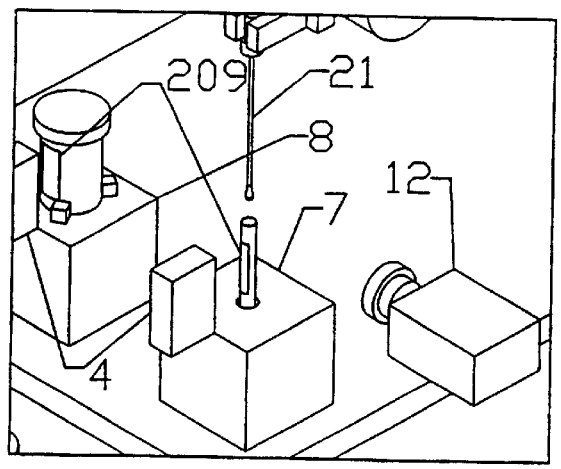
FIG. 1C is an enlarged pictorial view of FIG. La showing the removal of a swab from its tube.
Figure 1B:
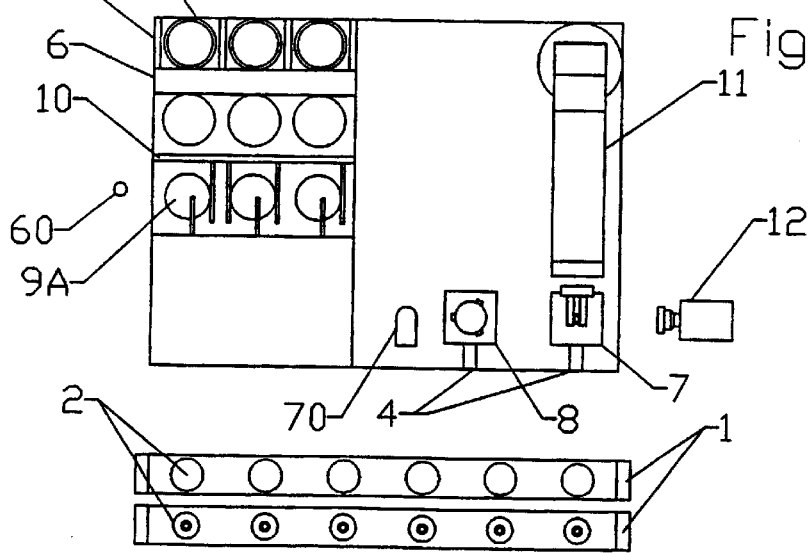
FIG. 1B is a plan view of FIG. 1A.

Referring generally to the drawings, FIGS. 1A and 1B illustrate the automated system having a conveyor system 1 for transporting specimen containers 2 into the system. The manipulating device 11 in the form of a robotic arm is used to grasp a specimen container 2 and move it in front of a specimen identification device 4. Electronic data from a label 209 on the specimen container read by the specimen identification device 4 is used to determine the type of culture medium plate 9 to be ejected from the plate dispenser 5.

The plate delivery system 10 carries the culture medium plate 9 to the plate identification device 6 which applies a label to the plate container. The robotic manipulating device 11, depending on whether it picks up a "swab type" holder or a "jar-type" holder, places the specimen container into either a "swab-type" holder 7 or a "jar-type" holder 8. The selection of a "swab-type" holder or a "jar-type" holder can be made manually, or under the control of a computer or other selecting device. The manipulating device 11 removes the cap from the specimen container. A "swab-type" stem 21 is presented to a tip location device 12 and then swings the swab stem 21 to the culture medium plate 9 which is inoculated. A "jar-type" specimen will have a specified amount of liquid extracted using a pipette 70 which is picked up by the manipulator and moved to inoculate the culture medium plate 9 that has been placed at the inoculation station 68.

Handling of a swab-type container is shown in FIGS. 2 and 4A through 6B wherein the cap 22 and swab stem 21 are depicted, initially within, and then being removed from the test-tube receptacle 20. FIG. 4C shows the cap 22 and swab stem 21 entirely removed from the test-tube receptacle 20 and demonstrates the possible tip 21A displacement of the swab stem 21.

Figure 5:
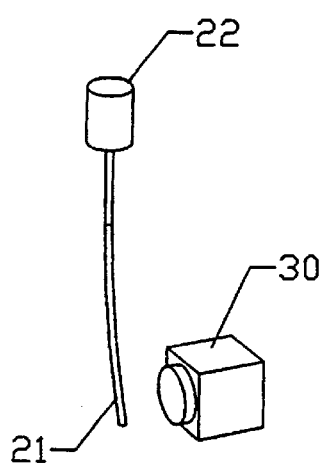
FIG. 5 is a pictorial depiction of the viewing of a swab to determine the location of its tip.

FIG. 5 shows the cap 22 and swab stem 21 as they are being presented to a camera-based tip location device 30.

Figure 7:
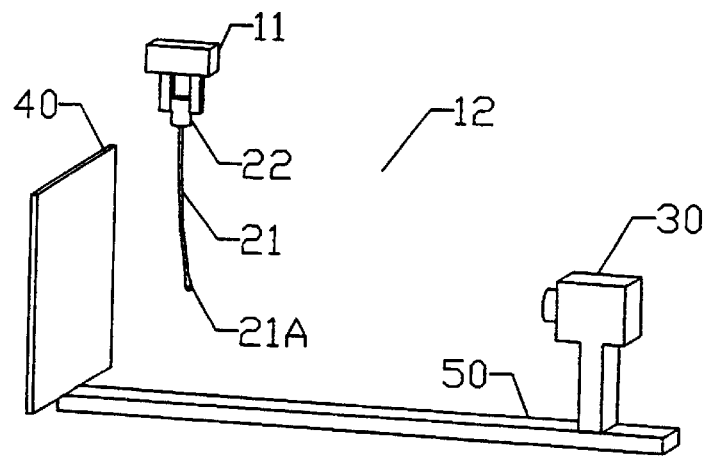
FIG. 7 is a pictorial depiction of a video camera viewing a swab suspended by a robotic gripper against a back lit surface panel.

FIG. 7 shows the perspective view of the double snapshot tip location setup 12. This embodiment consists of the manipulating device 11 which grasps the cap 22 attached to one end of the swab stem 21. The manipulating device 11 moves the swab stem 21 to a position between a camera 30 and a back light panel 40. The camera 30 and back light panel 40 are rigidly fixtured by a mounting bracket 50. The first snapshot is taken by the electronic camera 30, the manipulating device 11 rotates the cap 22 and swab stem 21 through 90° about the long axis of the cap 22, and then the second snapshot is taken. The images so obtained are then electronically processed in a digital computer control unit 344 to determine the location in space of the tip 21A with respect to the gripper 66 attached to manipulator 11.

Figure 8:
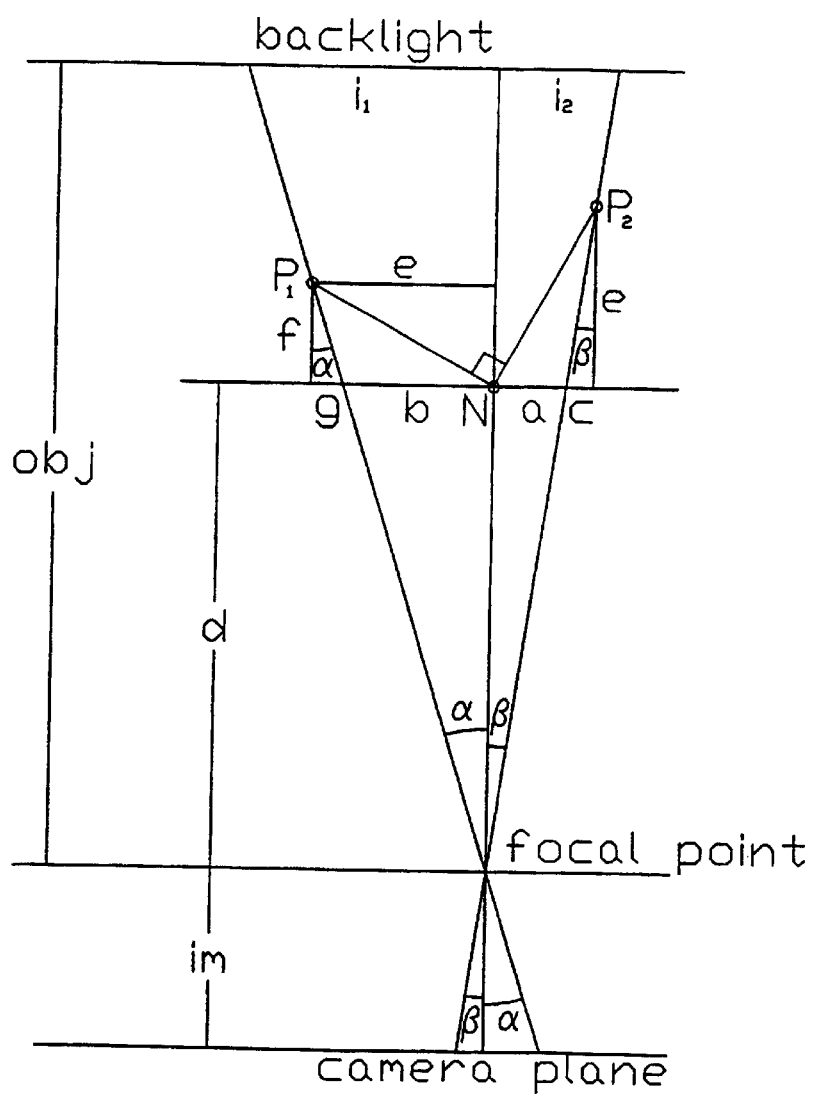
FIG. 8 is a plan view of the geometry for the extraction of the location of the swab tip being viewed in FIG. 7.

FIG. 8 shows the geometric layout of the double snapshot tip location setup 12. The pertinent angles and distances are defined and the accompanying equations can be found in Equation Sets 1 and 2 included hereafter. These equations are used by the computer to solve for the tip location.

Figure 9:
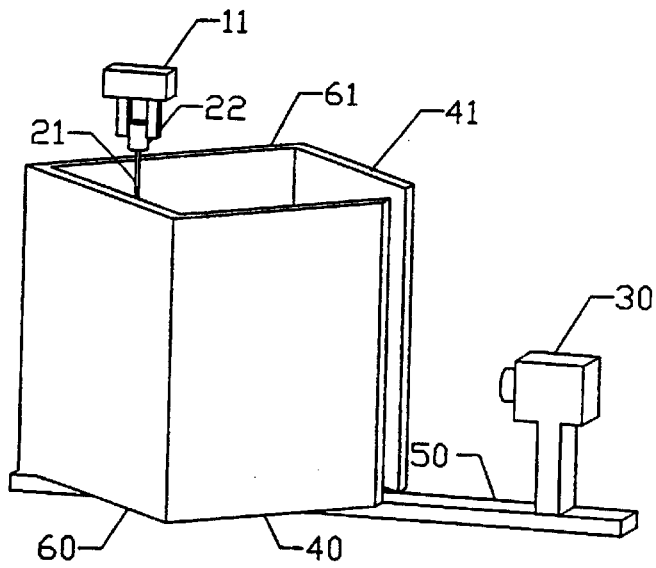
FIG. 9 is a pictorial depiction of a video camera viewing a swab suspended by a robotic gripper against a series of mirrored rear panels.

FIG. 9 shows a perspective view of the single snapshot tip location setup. This embodiment consists of a manipulating device 11 which grasps the cap 22 attached to one end of the swab stem 21. The manipulating device 11 moves the swab stem 21 to a position between a camera 30 with dual back light panels, 40,41 mounted on either side of the camera 30, and two mirrors, 60,61 positioned to form an enclosure around the swab stem 21. The mirrors are angled to each other at 90°. The camera 30 is placed such that its optical axis bisects the angle formed by the two mirrors 60, 61. Back light panel 41 is placed to form a 90° angle with mirror 61 and back light panel 40 is placed to form a 90° angle with mirror 60. The back light panels 40,41 must be narrow enough to leave a gap through which the camera 30 can view the mirrors 60, 61.

Figure 10:
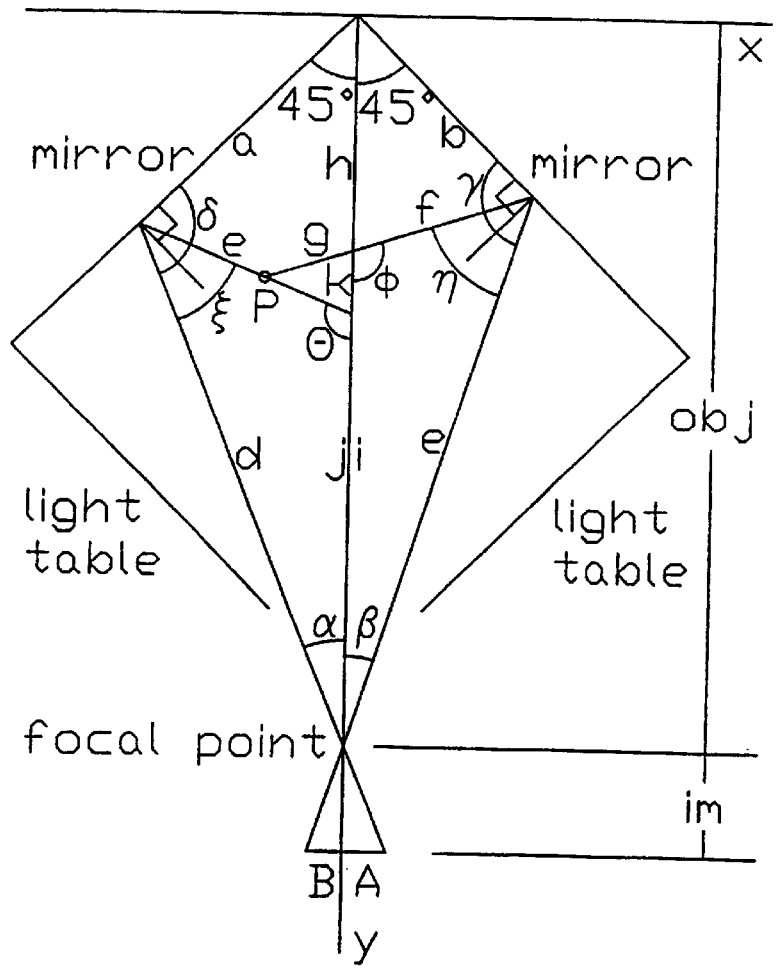
FIG. 10 is a plan view of the geometry for the extraction of the location of the swab tip being viewed in FIG. 9.

FIG. 10 shows the geometric layout of the single snapshot tip location setup. The pertinent angles and distances are defined and the accompanying equations can be found in Equation Set 2. From the input locational data obtained by camera 30 for the tip 21A, the location of the tip is solved by the computer using Equation Set 2.

Equation Set 1:

N = The nominal elongate element tip positions.

$P_1$ = Snapshot 1 elongate element tip position.

$P_2$ = Snapshot 2 elongate element tip position.

$$\tan \alpha = \frac{i_1}{obj}; \quad \tan \beta = \frac{i_2}{obj} \quad a = d\tan\beta; \quad b = d\tan\alpha$$

$$\frac{g}{a+c} = \tan \alpha; \quad \frac{c}{b+g} = \tan \beta \quad c = \frac{a(\tan\alpha + b)\tan\beta}{1 - \tan\alpha\tan\beta};$$

$$e = b + g \quad f = a + c$$

Equation Set 2:

$$\alpha = \tan^{-1}\left[\frac{A}{im}\right];$$

$$\beta = \tan^{-1}\left[\frac{B}{im}\right] \quad \gamma = 135 - \beta; \quad \delta = 135 - \alpha$$

$$\xi = 90 - 2\alpha; \quad \eta = 90 - 2\beta \quad \theta = 90 + \alpha;$$

$$\phi = 90 \div \beta \quad k = i - j;$$

$$h = obj - i \quad d = \frac{\sin 45 \times obj}{\sin \delta}; \quad c = \frac{\sin 45 \times obj}{\sin \gamma}$$

-continued $$i = \frac{\sin \eta \times c}{\sin \phi}; \quad j = \frac{\sin \xi \times d}{\sin \theta} \quad g = \frac{k \times \sin(90 - \alpha)}{\sin(\alpha + \beta)}$$

P = The tip position $\beta < \alpha$;

$$P = (h + g\cos(90 - \beta), -g\sin(90 - \beta)$$

$$\beta > \alpha; \quad P = (h + g\cos(90 - \beta), g\sin(90 - \beta)$$

Figure 11:
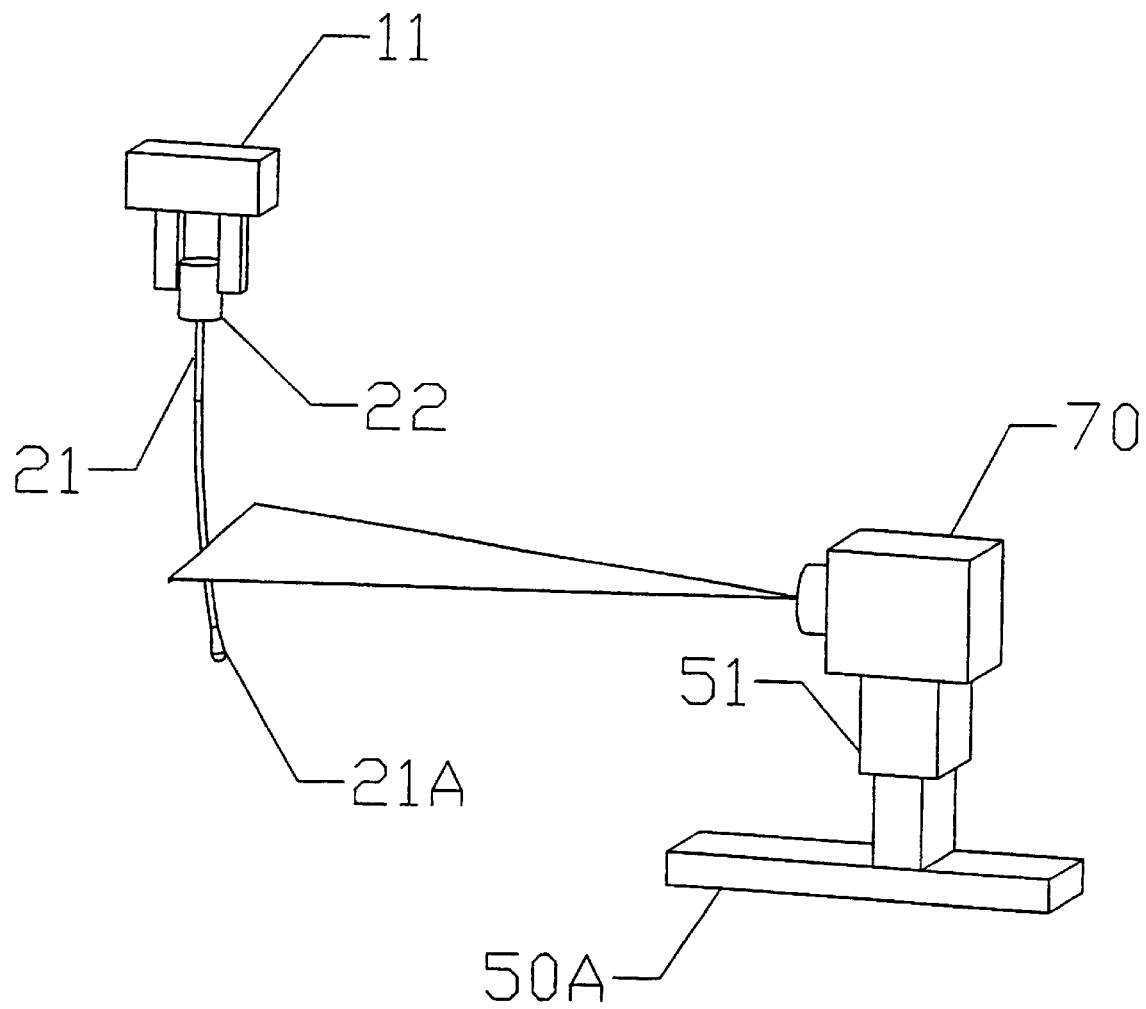
FIG. 11 is a pictorial view of a laser/ranger video camera extracting the location of a swab tip in space.

FIG. 11 shows a perspective view of the alternate laser range camera tip location setup. This embodiment consists of a manipulating device 11 which grasps the cap 22 attached to one end of the swab stem 21. The manipulating device 11 moves the swab stem 21 to a position in front of the laser range scanning camera 70. The laser range camera 70 is mounted on a linear slide 51 which is attached to a mounting bracket 50A. The linear slide 51 moves the laser range scanning camera 70 vertically while it collects data on range to the swab stem 21 which is compiled into a profile of the element tip. An alternative setup would have the camera 70 rigidly attached to the mounting bracket 50A and the scan would be accomplished by having the manipulating device 11 move the swab stem 21 with a straight line motion in the vertical direction. In either case, the location of the tip 21A in space may then be determined by the computer.

Figure 2:
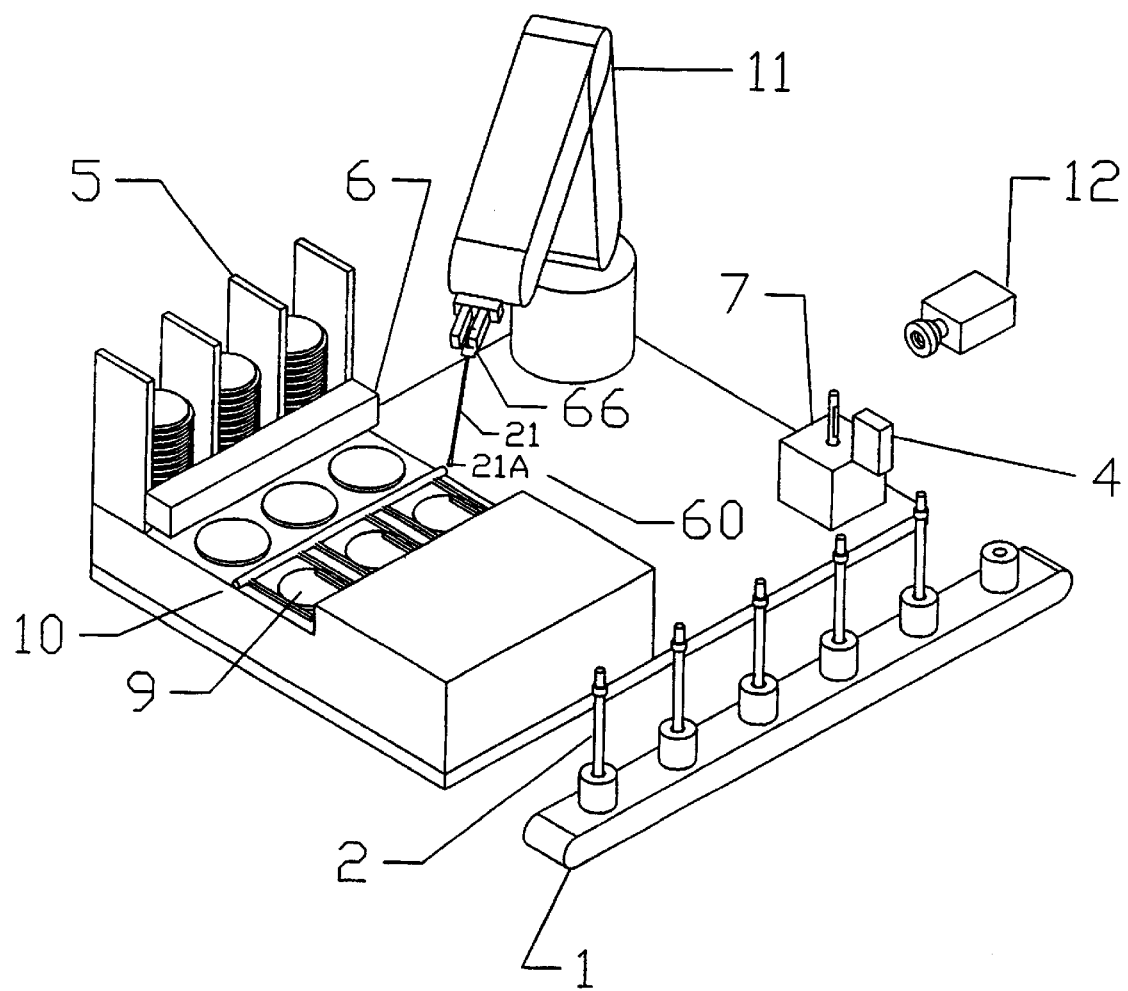
FIG. 2 is a pictorial view of an inoculating and streaking apparatus for handling swab-type specimens.

In FIG. 2 the manipulator 11 has carried the swab stem 21 with its tip 21A to the inoculation station 68 holding one or more culture plates 9. Multiple plates having differing culture media may sometimes be specified by the requisitioning doctor.

The stem 21 also may be fixtured as shown in FIGS. 22A and 22B by a confining rod 61 that is slid down the stem 21 to centrally position the tip 21A about the axis 62 for rotation of the cap 22.

Alternately, grasping fingers 63 may seize and center the stem 21 (FIGS. 23A, 23B).

Figures 24A, 24B, 24C:
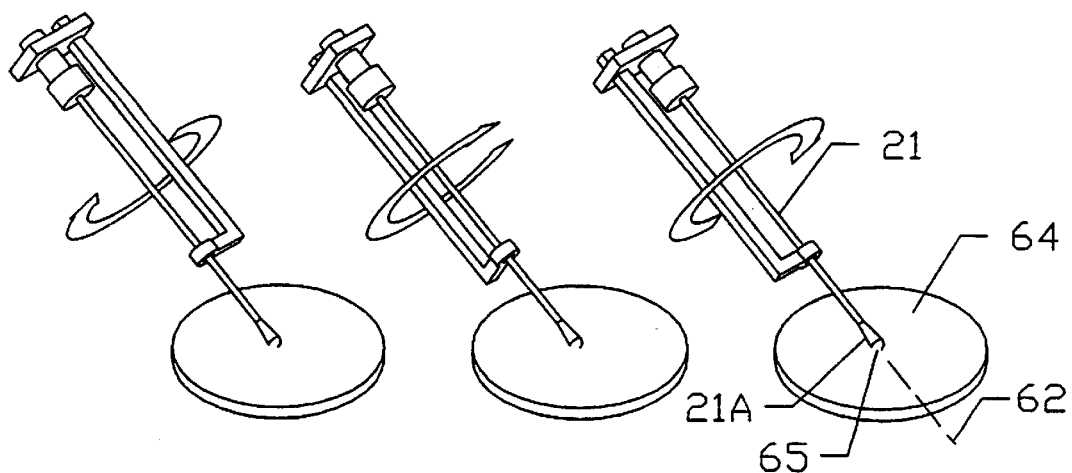
Figures 25A, 25B, 25C:
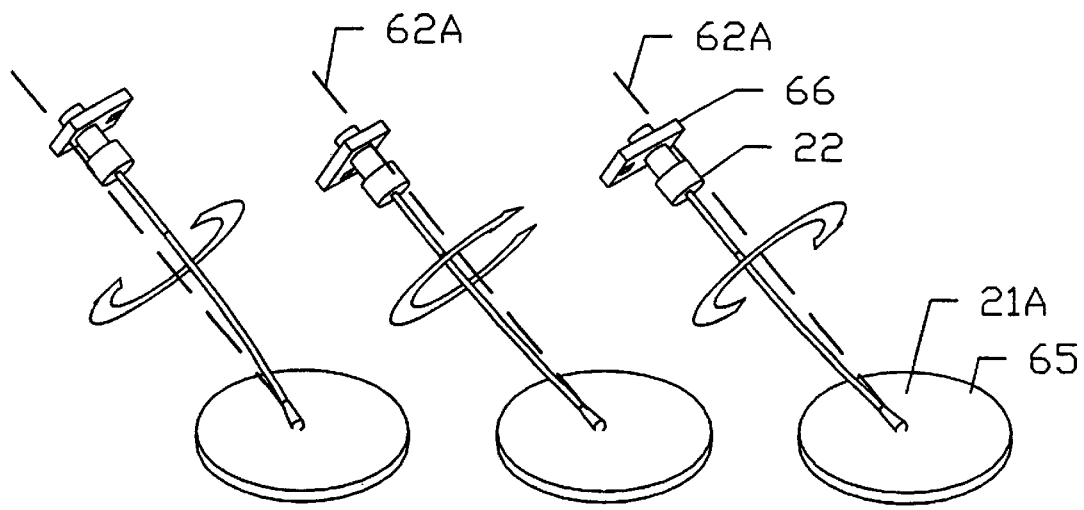

At the inoculation station 68 (FIG. 1B) the swab tip 21A is presented to the surface 64 of the culture medium in the plates 9 in either of the manners shown in FIGS. 24A through 25C. In FIGS. 24A through 24C the swab stem 21 is rotated about the axis of the stem to roll the tip 21A on the surface 64 at the deposit location 65. Alternatively, as shown in FIGS. 25A through 25C the gripper 66 on manipulator 11 may be displaced in space while the cap 22 is rotated, under the control of the computer control unit 344, ensuring that the tip 21A rotates about a constant axis 62A at the deposit location 65. The deposit location 65 is predetermined and is located by the computer controlling the movement of the swab tip 21A, or the pipette 70. This location 65 can, of course, be stored in a memory and can be associated with sample identity and the particular culture medium plate 9.

Figure 6A:
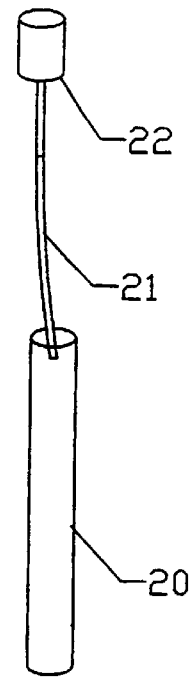
FIGS. 6A and 6B depict pictorially the reinsertion of the swab into its tube.
Figure 6B:
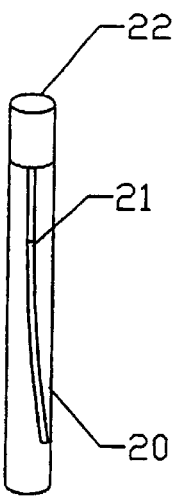

FIG. 6A shows the cap 22 and swab stem 21 with the tip 21A of the swab stem 21 being returned to its tube 20, being centred above the open end of the test-tube receptacle by the end effector/gripper 61 of the manipulating device 11, again under control of the computer control unit 344. In FIG. 6B the cap 22 and swab stem 21 have been completely replaced in the test-tube receptacle 20.

Figure 12:
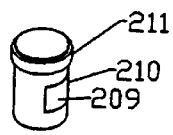
FIG. 12 is an isometric view of a "jar-type" specimen container carrying identifying indicia on its side.

FIG. 12 illustrates a "jar-type" specimen container having a jar- or bottle-like vessel or receptacle 210, a separate cap 211 which may be affixed to the receptacle and an area 209 which has been imprinted, encoded or otherwise embedded with pertinent information regarding the specimen.

Figure 13:
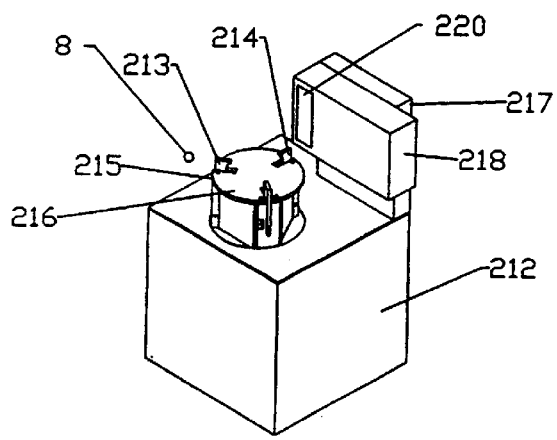
FIG. 13 is an isometric view of a part of one form of uncapping and data-reading apparatus for use with a jar-type container.

FIG. 13 illustrates one type of holder/reader apparatus 8 with a motor enclosure 212, three slender grasping fingers 213, 214 and 215 and the container platform 216 used for decapping a jar. The scanner device 218 is mounted on the support bracket 217.

Figure 14:
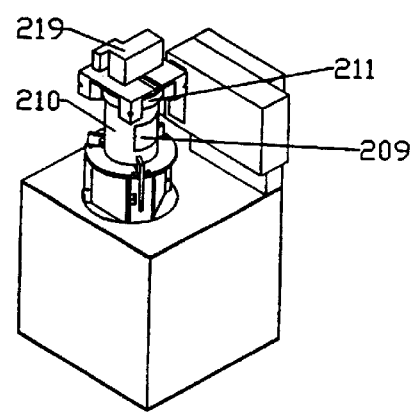
FIG. 14 is an isometric view of the uncapping and data reading apparatus of FIG. 13 with the lid grasped by a lid holder and the capped jar body held in place by the jar manipulating device.

FIG. 14 illustrates how the cap 211 of the specimen container is grasped by the cap removal device 219 after the jar 210 is placed on the container platform 216. The grasping fingers 213, 214 and 215 close about the container receptacle 210 and the jar 210 is rotated.

Figures 15, 16, 17:
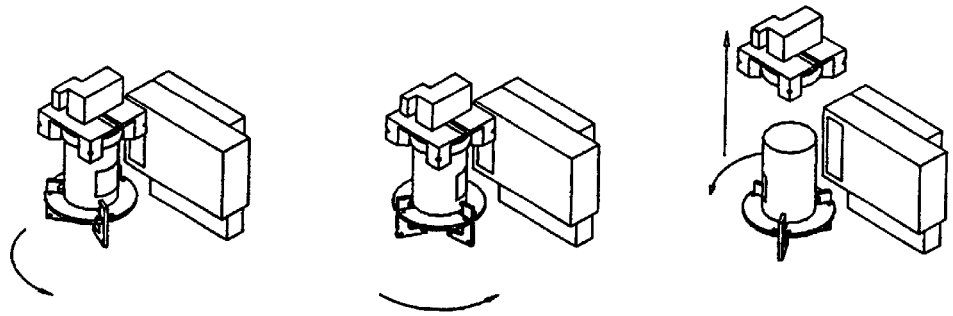
FIGS. 15–17 are sequential isometric views of the uncapping and data reading apparatus of FIG. 13 as the jar is uncapped and the data is read.

FIGS. 15–17 illustrate the rotational motion of the platform 216 and fingers 213, 214, 215 which cause the receptacle 210 to turn as well. Once the cap 211 and container 210 are disengaged, the manipulating device 219 moves the cap 211 with a positive vertical motion allowing the cap 211 and receptacle 210 to become separated. At the same time, the rotational motion of the receptacle 210 will cause the imprinted area 209 to be presented to the window 220 reading device 218 at some point during the revolution to effect recordal of the indicia thereon. The liquid specimen contained within the jar 210 may then be sampled to inoculate a culture medium.

After retrieval of a sample, the cap 211 is replaced on the receptacle 210 by the reverse activation of the cap removal device 219.

Figure 18:
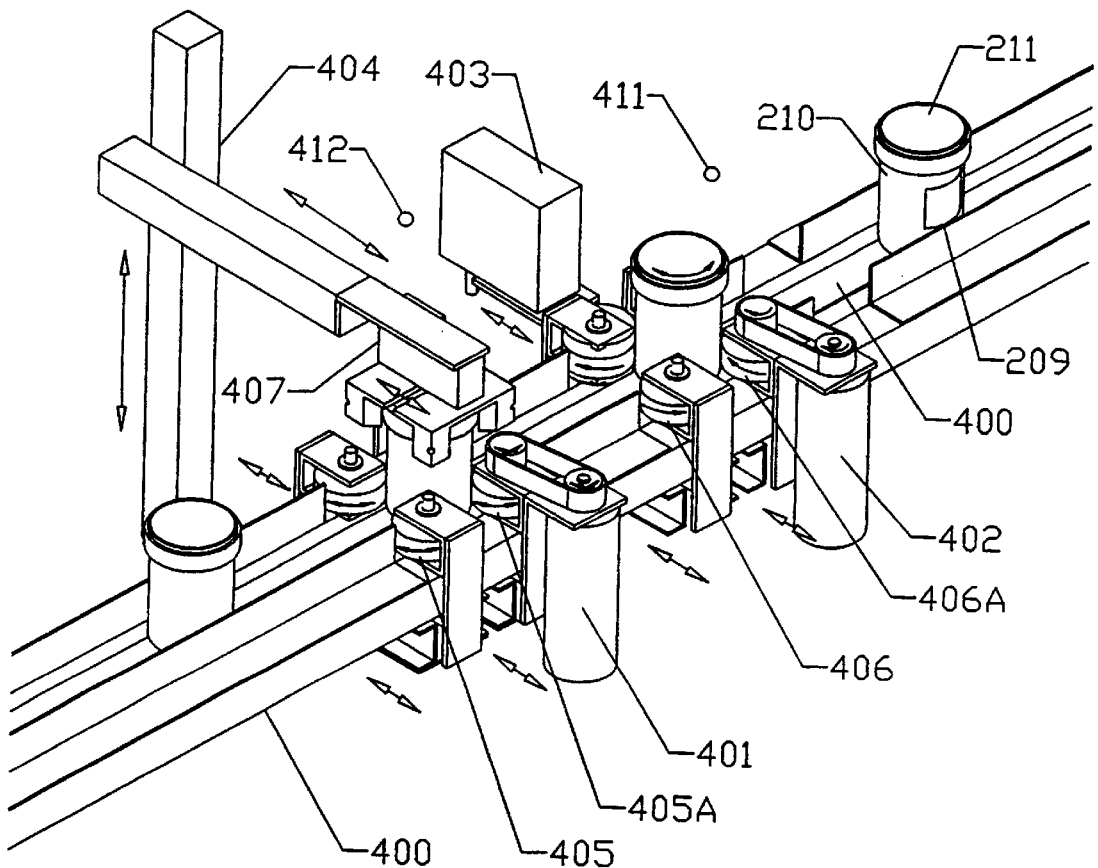
FIG. 18 is a pictorial view of jar-type containers being delivered on a conveyor to a de-capping station.
Figure 19:
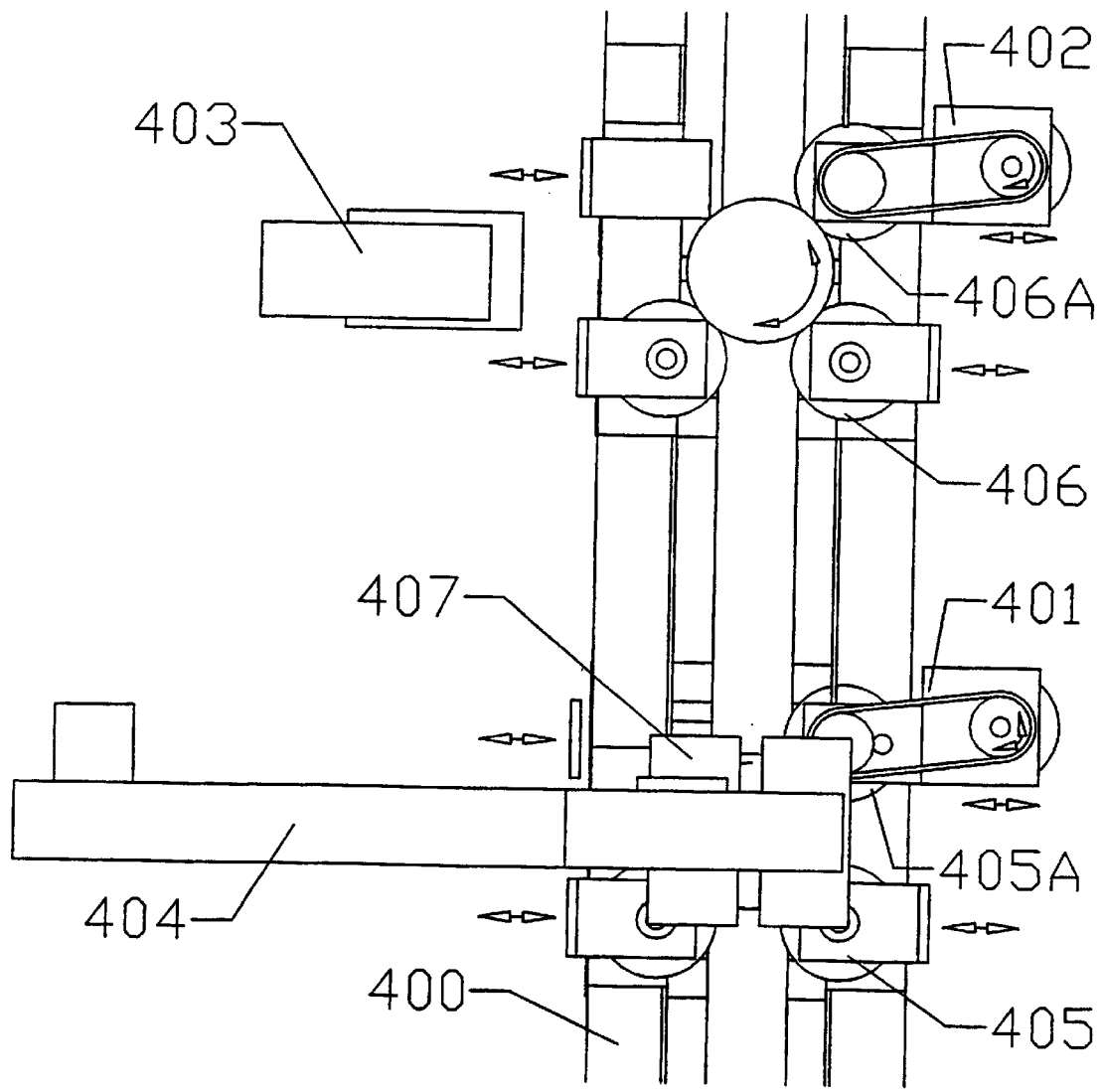
FIG. 19 is a plan view of FIG. 18.

An alternate decapping mechanism for jars is shown in FIGS. 18 and 19.

A jar 210 carried on a conveyor 400 is delivered to a reading station 411 where the jar 210 is grasped by four rollers 406, one of which, 406A, is driven by motor 402. As the jar 210 is rotated by the powered roller 406A, the indicia 209 carried on its side are read by the reader 403. Throughout rotation the jar 210 remains on the conveyor 400. One form of indicia could be a bar code, which can provide an indication of the streak pattern.

The jar 210 is then advanced by the jar conveyor 400 to a de-capping station 412. There rollers 405 again grasp the jar 210 while a cap-holding mechanism 407 grasps the cap 211. One of the rollers 405A driven by motor 401 rotates the jar body while the cap 211 is held against rotation by the cap-holding mechanism 407. Once sufficient rotation has occurred to effect disengagement, the cap 211 is raised from the jar 210 and the cap-holding mechanism 407 retires from the de-capping site 412 carrying the cap 211 with it. This exposes the specimen contents of the jar 210 for removal of a sample. After retrieval of a sample, the cap is repositioned over the receptacle by mechanism 407 and rotation of the receptacle, in a reverse direction by roller 405A reapplies the cap.

Figure 3:
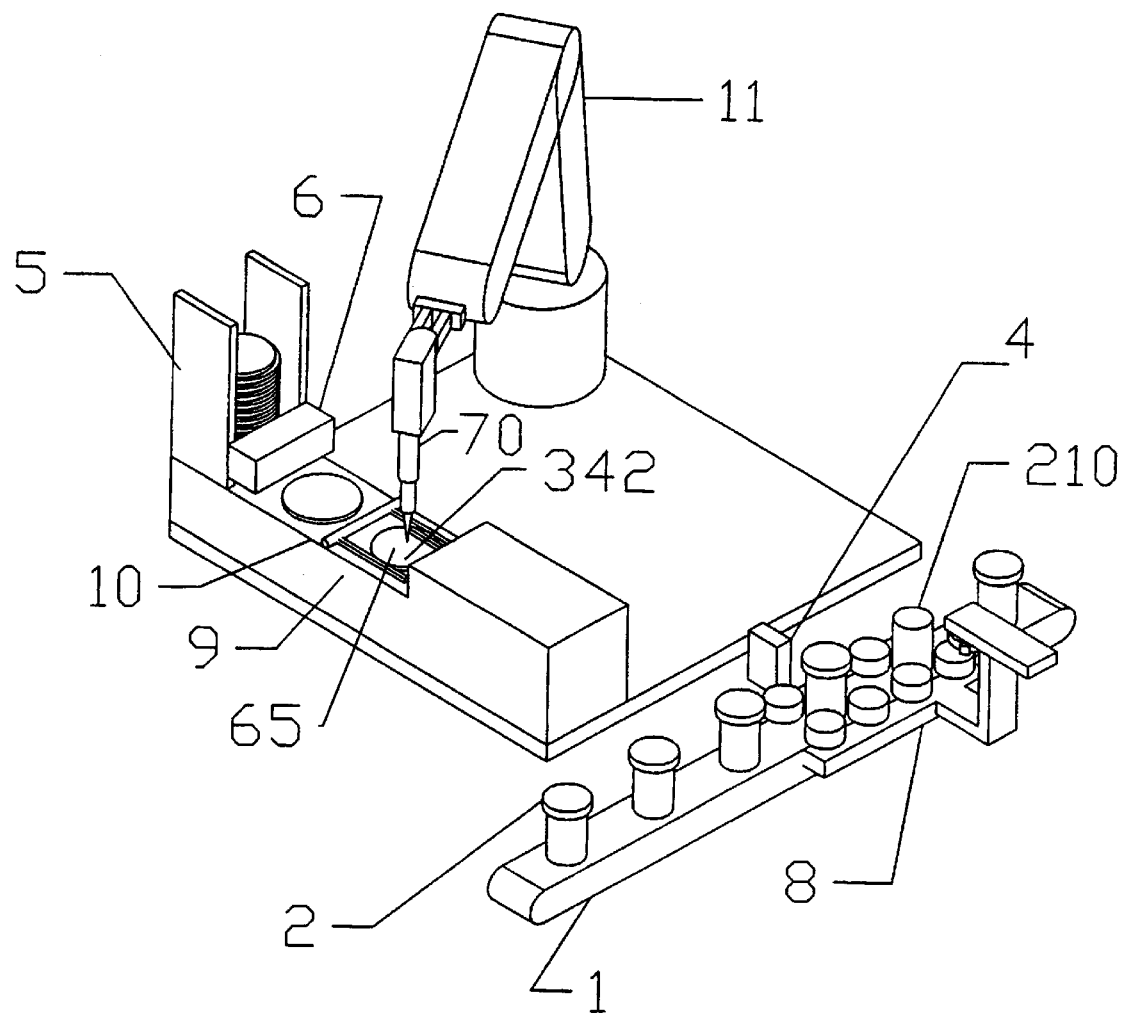
FIG. 3 is a pictorial view of an inoculating and streaking apparatus for handling jar-type urine samples.
Figure 4A:
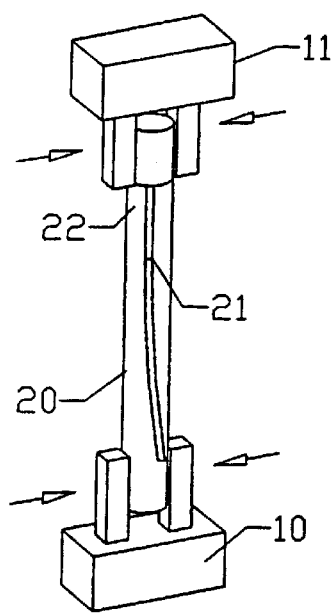
FIGS. 4A through 4C are successive pictorial depictions of the removal of a swab from a tube.
Figure 4B:
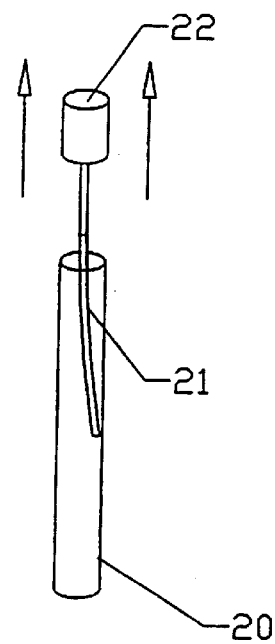
Figure 4C:
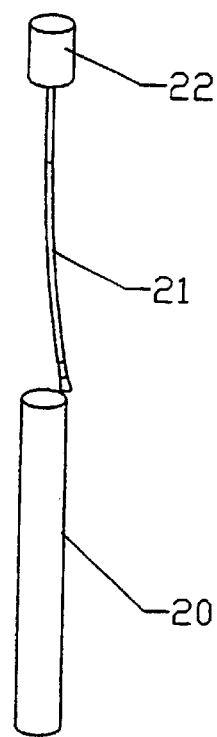

As shown in FIG. 3 the manipulator 11 grasps a pipette 70 from its storage station and extracts a quantity of liquid from the opened container 210. This liquid is then placed on the agar surface 64 on the plate 9 at a deposit location 65. The manipulator then moves the pipette to a disposal station (not shown) where the pipette tip is discarded and a new sterile tip installed. The pipette 70 is then used again or returned to its storage station in the case of the versatile swab/jar system of FIG. 1A when a swab is next in line for inoculation.

Figure 20:
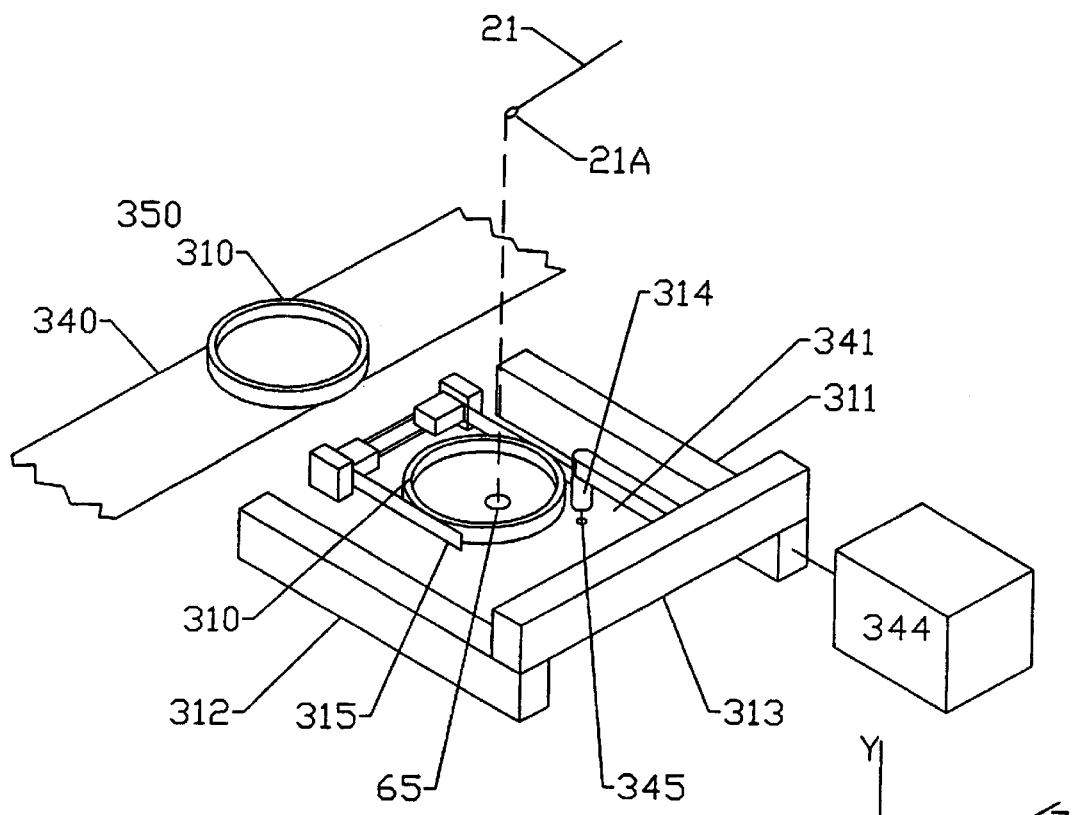
FIG. 20 is an isometric view of the delivery of culture medium dishes to the inoculation location of the streaking apparatus.

FIG. 20 illustrates the delivery of a culture medium container (in the form of a plate 310) carried on a conveyor 340, or dispensed by a plate dispenser as at 5 in FIG. 1A, to a transfer location 350 opposite an inoculation and streaking station 341. The culture medium plate 310 is inverted at the transfer location 350 with its lid on the downward side. Two clamping arms 315, 316 rotationally transfer the plate 310, without its lid and containing an agar or similar coating, to the inoculation and streaking station 68 with its agar coated surface 64 upwardly exposed. Alternatively, the rotational arms may be outfitted with suction cups to separate the plate from its lid.

Figure 21:
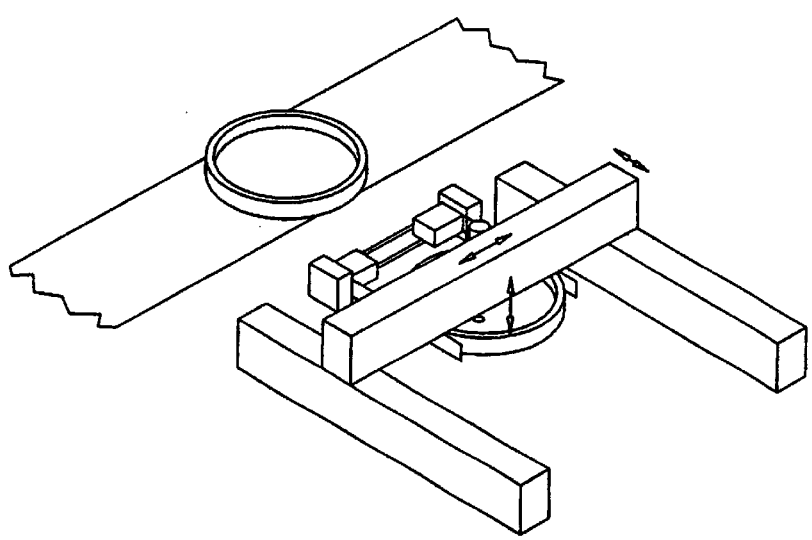
FIG. 21 is an isometric view of the inoculation location of FIG. 20 with the streaking mechanism in position over the exposed culture medium to effect streaking.

At the inoculation and streaking station 341 rails 311, 312 support a cross motion beam 313 which, in turn, carries the streaking tool 314. As shown in FIG. 21 the rails 311, 312 provide for effecting motion in the +/− X direction. Cross motion beam 313 supports the streaking tool 314 and provides for motions in the +/− Y and +/− Z directions.

Figure 26:
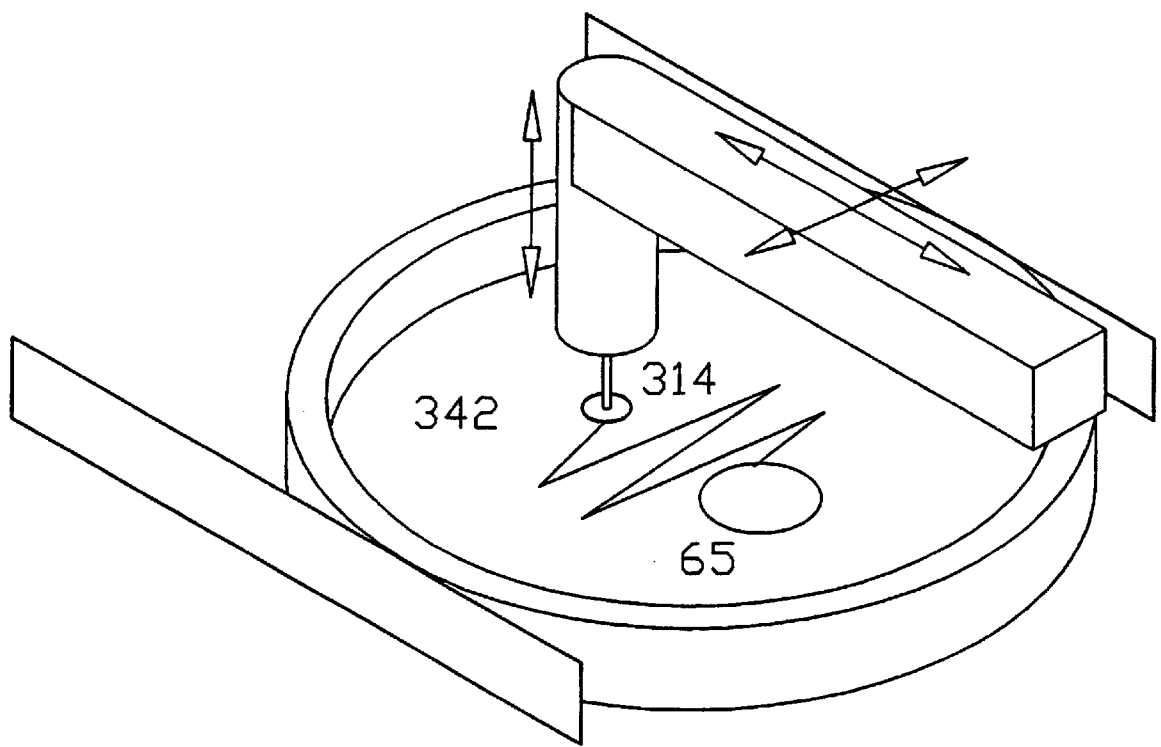
FIG. 26 illustrates one form of streak pattern.

Streaking, as shown in FIG. 21 and 26, occurs by the presentation of the streaking tool 314 to the deposit location 65, once the plate 310 has received the transfer of its bacterial specimen as in FIG. 21. Once the sterile tip portion 345 of the streaking tool 314, enters onto the agar surface 64 at the deposit location 65, the tool 314 executes a streaking pattern, controlled by the computer control unit 344 (FIG. 20) that corresponds with the specimen's identification. Since the streaking tool 314 is mounted on an actuated platform that can produce relative motion between the arm 313 and the plate 310 in two independent directions, it is made to move through a user-defined, two-dimensional pattern that has been programmed into the streaking actuator's computer-managed control unit 344. Such a pattern can have been obtained from a bar code on the container 2, and one form of pattern 351 is shown in FIG. 26.

The tip 345 of the streaking tool 314 contacts the surface 64 of the culture medium at precisely the deposit location 65 based on the stored data carried within the computer control unit 344. This data corresponds to the location whereat the manipulator 11 effected deposit of the bacterial specimen which is also stored in the memory of the computer control unit 344. Once the tip 345 of the spreading head makes contact with the surface 64 of the culture medium the appropriate streaking pattern 351 is executed in response to commands from the computer control unit 344.

After the streaking operation, the culture medium plate 310 is returned to the lid. Where prescribed by the programmed protocol contained in the computer control unit 344, after execution of a first streaking pattern, the streaking tool 314 may be lifted until the head is clear of the culture medium's surface and another plate 310 with a fresh agar spreading surface 64 may be presented to the inoculation and streaking station 341. Further inoculation with the same specimen sample may then be optionally effected. Alternately, multiple plates 8 may be presented at parallel streaking stations as shown in FIGS. 1B and 2.

A feature of the streaker mechanism is that, due to its simple mechanical configuration and computer control system, the streaking head 314 as shown in FIGS. 20 and 26 spans a planar space that covers as much of the culture medium surface as is required, and is totally versatile as to the streaking patterns 351 it may execute. The streaking patterns 351 chosen may conveniently vary with and correspond to the identity of the specimen from which the culture being streaked was obtained.

Figure 27:
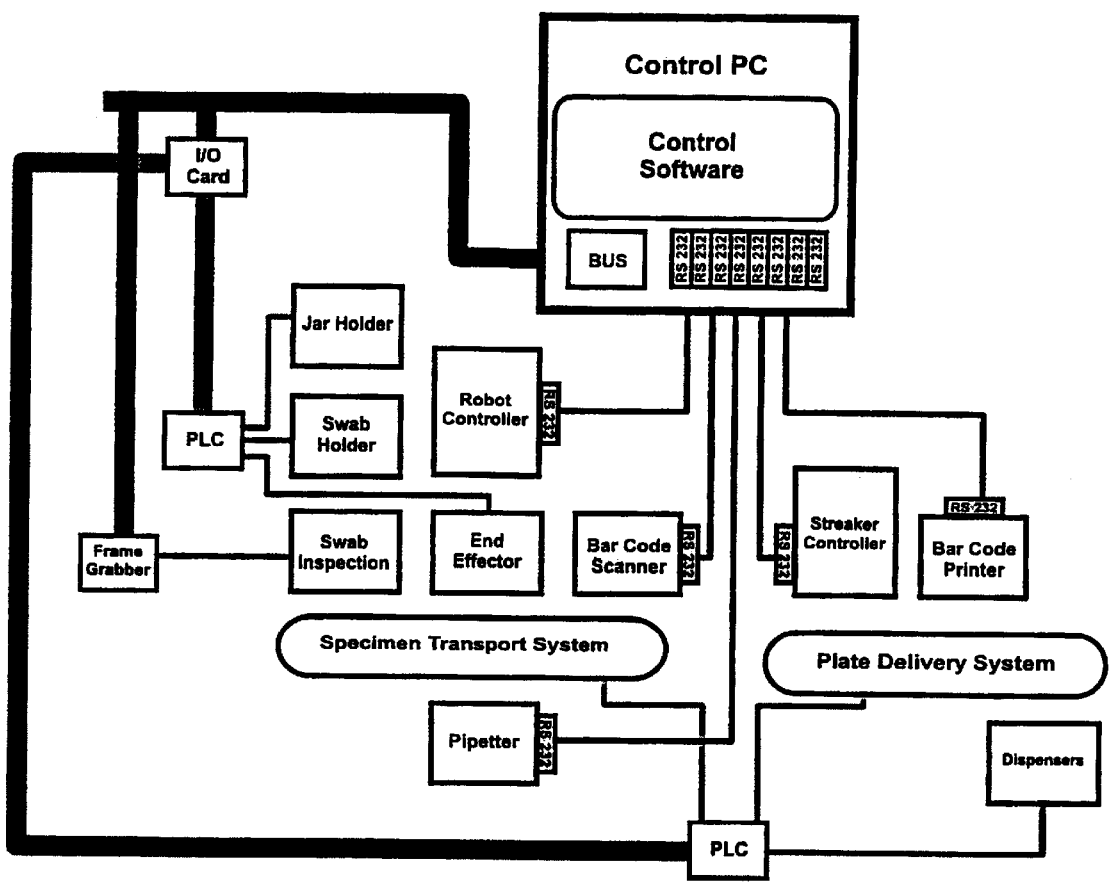
FIG. 27 is a schematic diagram of the control functions linking the active elements of the system to a digital controller.

FIG. 27 shows schematically the linkages between the various operating mechanism and the controlling sources that issue the necessary command signals.

It will be appreciated that the various movements of the several items would normally be controlled from a central controller, a computer control, and which would also receive and record various items of data obtained during operation. Thus for example, the positioning of the culture medium containers, the sample containers, the gripping mechanism, pipette mechanism, the viewing of the swabs of swab-type containers, the deposition of samples in the culture medium surface, the actuation of cap removal mechanisms, data reading systems, the streaking and other movements would be under control of the central controller, with feeding of data to and from the control. Positional and identifying data can be retrieved from the central control, as desired.

FIG. 27 is a diagrammatic representation of a control system, with various items linked. Some of the elements have been identified with appropriate references, relating to such elements in the previous disclosure. It will be understood that this diagrammatic representation is only typical and can vary without affecting the actual operation of the apparatus, this being controlled eventually by the control software. Particularly, the apparatus and method of the invention is flexible, and capable of handling both swab-type and jar-type specimen holders intermixed.

CONCLUSION

The foregoing has constituted a description of specific embodiments showing how the invention may be applied and put into use. These embodiments are only exemplary. The invention in its broadest, and more specific aspects, is further described and defined in the claims which now follow.

These claims, and the language used therein, are to be understood in terms of the variants of the invention which have been described. They are not to be restricted to such variants, but are to be read as covering the full scope of the invention as is implicit within the invention and the disclosure that has been provided herein.

What is claimed is:

1. An automated specimen container transport, handling and inoculating system for transferring a sample of a bacteria specimen from specimen containers to a culture medium, followed by streaking of said sample bacteria specimen over said culture medium comprising:
    (a) a specimen delivery system to convey a sample of the specimen from its original specimen container to a deposit location on a culture medium;
    (b) means for recording a position of said deposit location in a memory as deposit location data;
    (c) a streaking tool carried by a streaking mechanism; and
    (d) a controller for said streaking mechanism wherein said controller, using the recorded deposit location data to guide the streaking tool, directs the streaking tool to move to said culture medium and effect a streaking pattern over said culture medium.

2. A system as in claim 1 wherein said specimen containers contain differing specimen types and are each identified by specimen indicia corresponding to each specimen, said inoculating system further comprising an indicia reader for identifying the specimen indicia and for providing a specimen signal to the streaking mechanism, wherein the streaking pattern executed by the streaking tool is controlled by a signal from the controller that, based on the specimen signal of the indicia reader, conforms to a predefined pattern that corresponds to the identity of the specimen sample.

3. A system as in claim 1 wherein said specimen delivery system comprises a grasping manipulator in combination with a swab mounted at the end of a swab stem as a carrier for the sample specimen wherein the swab is carried to and positioned by the grasping manipulator at the deposit location.

4. A system as in claim 3 comprising:
    (a) a tip location device to which the swab and swab stem are presented by the grasping manipulator whereby the location of the swab with respect to the grasping manipulator is determined by a visual examination effected by the tip location device; and
    (b) a location memory accessible by the controller wherein the swab location with respect to the grasping manipulator is then stored,
whereby the stored swab location is subsequently used by the controller to control the specimen delivery system in positioning the swab on the culture medium at the deposit location.

5. A system as in claim 4, wherein said grasping manipulator includes means for rotating said stem to rotate said swab in contact with said culture medium and for moving an axis of rotation of said stem to offset distortion of the stem.

6. A system as in claim 4 wherein the controller of the specimen delivery system comprises control means for effecting reinsertion of the swab into a specimen container using the swab location data stored in the location memory of the controller to ensure that the swab passes into the specimen container without contaminating its exterior surface.

7. A system as in claim 3 wherein a grasping mechanism of said grasping manipulator provides an axis of rotation and the swab is mechanically fixtured to ensure that it is positioned along said axis of rotation by providing a guide to guide the swab into alignment with the axis of rotation during transfer of bacteria specimen to the culture medium.

8. A system as claimed in claim 1 in combination with a threaded, capped specimen container with identifying specimen indicia encoded on the side of the container comprising a container manipulating device including means for:
    (a) grasping the cap of the container while the container is rotated by a rotating container holder at a lid-opening station; and
    (b) raising and removing the cap of the specimen container to one side once the rotating container holder has rotated the container sufficiently so as to cause the cap and the container to disengage and wherein an indicia reader is located to one side of the rotating container holder to read said specimen indicia encoded on the side of the specimen container.

9. A system as in claim 1 wherein the specimen delivery system comprises:
    (a) culture holding means for holding a culture medium container with culture medium present therein at a predetermined inoculation position;
    (b) specimen container positioning means for positioning the specimen container at a specimen extraction station;
    (c) a specimen applicator for extracting a specimen sample from said specimen container, and
    (d) specimen transfer means for moving said specimen applicator to said culture medium and for depositing the specimen sample at the deposit location.

10. A system as claimed in claim 9, including means for locating the position of the specimen applicator in space upon its removal from a specimen holder.

11. A system as claimed in claim 9 wherein the specimen container carries specimen indicia data and said system comprises an indicia reader for reading data on said container.

12. A system as claimed in claim 9 wherein said specimen containers comprise swab containers, each having an elongate tubular receptacle, a cap with a stem extending from said cap into said receptacle, and a specimen sample holding swab positioned at the end of said stem remote from said cap, said specimen transfer means comprising a controlled gripping member for gripping and removing said cap from said receptacle and for moving said swab to position it at said deposit location on said culture medium.

13. A system as claimed in claim 12, including means for viewing said swab after removal from said receptacle and producing swab position data for the location of said swab with respect to said cap for use by the specimen transfer means in subsequently positioning the swab at the deposit location in accordance with said swab position data.

14. A system as claimed in claim 13, wherein said specimen transfer means comprises means to replace said swab in said tubular receptacle without contacting the swab against the exterior surface of the receptacle.

15. A system as claimed in claim 12, including straightening means for engaging with said stem after removal from said receptacle, to straighten any distortion in said stem.

16. A system as claimed in claim 12, said gripping member including means for rotating said stem to rotate said swab in contact with said culture medium and for moving an axis of rotation of said stem to offset distortion of the stem.

17. A system as claimed in claim 9, said specimen container comprising a container having a jar receptacle and a separate cap, said specimen applicator comprising a controlled gripping member and a pipette grasped by said gripping member, and said specimen transfer means further comprising control means for
    (a) moving said gripping member and pipette over said specimen holder to retrieve a specimen sample;
    (b) moving said gripping member and pipette over a culture medium container; and
    (c) depositing said specimen sample onto said culture medium at said deposit location.

18. A system as claimed in claim 12, said cap being a screw cap for threaded attachment to said jar receptacle, said system including means for rotating said cap relative to said receptacle at a cap removal station for removal of said cap.

19. A system as claimed in claim 18, wherein said jar receptacle carries specimen data and further including transfer means for transporting said jar receptacle through a data reading station including data reading means for reading said specimen data on aid jar receptacle at said data reading station, said means for moving said streaking tool during streaking being governed by said specimen data.

20. A system as claimed in claim 9, including means for positioning swab holders and jar holders, said specimen transfer means being adapted to remove said sample from either of said holders.

21. A method of automated deposition of a specimen sample on a culture medium, comprising:
    (a) providing a culture medium container delivery system and controllably delivering a culture medium container with culture medium present therein to a predetermined position constituting a streaking station;
    (b) providing a specimen container delivery system and controllably delivering a specimen container with a biological specimen contained therein to a specimen retrieval station;
    (c) providing a specimen transfer mechanism and controllably moving said specimen transfer mechanism to remove a specimen sample from a specimen container at the specimen retrieval station, convey the specimen sample to the streaking station and deposit said speciment sample onto the surface of the culture medium in said culture medium container at a deposit location on said surface of said culture medium;
    (d) recording the deposit location of the specimen sample on said surface of said culture medium in a memory as location data, and
    (e) providing a streaking tool and controllably moving said streaking tool, using the recorded location data to guide the streaking tool to the specimen sample, to move said streaking tool in a predetermined streaking pattern over said surface of said culture medium.

22. A method as claimed in claim 21, said specimen container comprising a swab container having an elongate tubular receptacle, a cap, a stem extending into said receptacle from the cap, and a swab positioned at the end of the stem, the swab holding the biological specimen sample, including the steps of:
    (a) moving said specimen transfer mechanism to grip said cap and remove said stem and said swab to a first position, before position sensing means, viewing said swab;
    (b) obtaining positional data relating to the spatial position of said swab with respect to said transfer mechanism; and
    (c) moving said stem and swab to deposit said sample on said surface of said culture medium at said deposit location, in conformity with said positional data.

23. A method as claimed in claim 22, including the further step of controllably moving said transfer mechanism to convey said stem and swab to said receptacle and insert the swab and stem into the receptacle without allowing the swab to contact the outside surface of the receptacle.

24. A method as claimed in claim 21, said specimen container comprising a container having a jar receptacle and a screw cap with liquid specimen present therein, including the steps of:
    (a) removing said cap at the specimen retrieval station;
    (b) controllably moving said specimen transfer mechanism to convey a pipette to said specimen container at the specimen retrieval station to retrieve a liquid specimen sample from said receptacle; and
    (c) moving said specimen transfer mechanism and pipette to deposit said liquid specimen sample onto said surface of said culture medium at said deposit location.

25. A method as claimed in claim 21 including the steps of reading identifying specimen data present on said container, recording said data and effecting a streaking pattern in the culture medium that corresponds to the specimen data.

26. A method as claimed in claim 21, including
    (a) moving said containers along a conveying system to position said containers sequentially at a viewing station;
    (b) reading identifying specimen data carried on each of the containers, while the container is present at the viewing station; and
    (c) conveying said containers sequentially to the specimen retrieval station, and subsequently using the specimen data to define the streaking pattern.

27. An automated culture inoculation system for transferring a sample of a bacterial specimen from specimen containers to a culture medium, followed by streaking of such sample bacteria specimen over said culture medium comprising:
    (a) a culture medium container delivery system to controllably deliver a culture medium container with culture medium having an exposed surface present therein to a predetermined position constituting a streaking station;
    (b) a specimen container delivery system to controllably deliver a specimen container with a biological specimen contained therein to a specimen retrieval station;
    (c) a specimen transfer mechanism positioned to controllably remove a specimen sample from a specimen container at the specimen retrieval station, convey the specimen sample to the streaking station and deposit said specimen sample onto the surface of the culture medium in said culture medium container at a deposit location on the surface of said culture medium;

(d) data recording means for recording the deposit location of the specimen sample on said surface of said culture medium in a memory as location data;

(e) a streaking tool; and (f) control means for controllably moving said streaking tool, using the recorded location data, to guide the streaking tool to engage with the specimen sample present on the surface of said culture medium, and move said streaking tool in a predetermined streaking pattern over said surface of said culture medium.

\* \* \* \* \*